(12) United States Patent
Wilson (10) Patent No.: US 12,201,462 B2
(45) Date of Patent: Jan. 21, 2025

(54) PATIENT IMAGING AND TREATMENT TABLE EXTENSION WITH INTEGRATED HANDRAILS

(71) Applicant: Medtec LLC, Orange City, IA (US)

(72) Inventor: Roger F. Wilson, Sarasota, FL (US)

(73) Assignee: Medtec LLC, Orange City, IA (US)

( * ) Notice: Subject to any disclaimer, the term of this patent is extended or adjusted under 35 U.S.C. 154(b) by 270 days.

(21) Appl. No.: 17/784,777

(22) PCT Filed: Dec. 17, 2020

(86) PCT No.: PCT/US2020/065563
§ 371 (c)(1),
(2) Date: Jun. 13, 2022

(87) PCT Pub. No.: WO2021/127151
PCT Pub. Date: Jun. 24, 2021

(65) Prior Publication Data
US 2022/0409151 A1    Dec. 29, 2022

Related U.S. Application Data

(60) Provisional application No. 62/949,090, filed on Dec. 17, 2019.

(51) Int. Cl.
*A61B 6/04*     (2006.01)
(52) U.S. Cl.
CPC .................... *A61B 6/0435* (2013.01)
(58) Field of Classification Search
None
See application file for complete search history.

(56) References Cited

U.S. PATENT DOCUMENTS

| 5,386,447 A | 1/1995 | Siczek |
| 5,778,467 A | 7/1998 | Scott et al. |
| 5,820,552 A | 10/1998 | Crosby et al. |

(Continued)

FOREIGN PATENT DOCUMENTS

| JP | 3601192 B2 | 12/2004 |
| JP | 2017-12448 A | 1/2017 |

(Continued)

OTHER PUBLICATIONS

PCT International Search Report issued for the corresponding international application No. PCT/US2020/065563 mailed on Apr. 19, 2021, 11 pages.

*Primary Examiner* — Marcus H Taningco
(74) *Attorney, Agent, or Firm* — Snyder, Clark, Lesch & Chung, LLP (57) ABSTRACT

A patient treatment table for prone patient breast examination and treatment is described. The table may be in the form of a table base and table extension, the table extension being removably attached to the table base. The patient treatment table extension includes one or more hand rails for grasping by the patient above and along one or both longitudinal sides of the device to assist the patient in getting onto the treatment table. The handrails are mounted such that they can be removed or swung out of the way of medical equipment once the patient is positioned on the table. The table may also be in the form of a couch-top overlay.

20 Claims, 9 Drawing Sheets

(56) References Cited

U.S. PATENT DOCUMENTS

| | | |
|---|---|---|
| 6,922,859 B2 | 8/2005 | Gagnon et al. |
| 8,382,371 B2 | 2/2013 | Yoshida et al. |
| 8,406,846 B2 | 3/2013 | Yoshizawa et al. |
| 9,615,796 B2 | 4/2017 | Coucke |
| 10,045,698 B2 | 8/2018 | Angott et al. |
| 10,130,541 B2 | 11/2018 | Albanese et al. |
| 2013/0198960 A1 | 8/2013 | Angott |
| 2014/0121499 A1 | 5/2014 | Coppens et al. |
| 2017/0028218 A1 | 2/2017 | De Neve |
| 2017/0112410 A1 | 4/2017 | Menon |

FOREIGN PATENT DOCUMENTS

| | | | | |
|---|---|---|---|---|
| WO | WO-9802095 A1 * | 1/1998 | ......... | A61B 17/3403 |
| WO | 2004041089 A2 | 5/2004 | | |
| WO | WO-2013041994 A2 * | 3/2013 | ......... | A61B 10/0041 |
| WO | 2014160706 A | 10/2014 | | |
| WO | 2017142747 A1 | 8/2017 | | |
| WO | 2018/006295 A1 | 1/2018 | | |

\* cited by examiner

PATIENT IMAGING AND TREATMENT TABLE EXTENSION WITH INTEGRATED HANDRAILS

CROSS REFERENCE TO RELATED APPLICATIONS

This application claims priority under 35 U.S.C. § 119 to U.S. Provisional Patent Application No. 62/949,090 filed on Dec. 17, 2019, entitled Patient Imaging and Treatment Table Extension with Integrated Handrails, the contents of which are hereby incorporated herein by reference in their entirety.

BACKGROUND

Prone breast treatment patient tables place a high physical demand on the patient to manage lowering themself face down onto the device and up again. This difficulty is exacerbated by a number of factors. First, patients typically indicated for use of prone devices are most often older, large, and not especially athletic or agile women. Such devices are necessarily narrow to fit scanning machines and include a large opening on one side which further limits the patient's ability to find a stable, secure hand grasp/rest for hand walking themselves outward and downward onto the device. With current devices, if a patient starts to lose her balance and fall forward, or worse to the side, there is little she could do to keep from falling, relying almost exclusively on the clinical technician to catch her and keep her on the device. A cantilevered extension table that projects out into an open space can make the patient even more anxious about being suspended without adequate grasping means to feel secure.

DETAILED DESCRIPTION OF PREFERRED EMBODIMENTS

Those skilled in the art will recognize other detailed designs and methods that can be developed employing the teachings of the present invention. The examples provided here are illustrative and do not limit the scope of the invention, which is defined by the attached claims. The following detailed description refers to the accompanying drawings. The same reference numbers in different drawings may identify the same or similar elements.

In an aspect of the invention, a prone breast treatment table extension includes two hand rails for grasping by the patient above and along each longitudinal side of the device. With the addition of these hand rails, patients are provided a simpler, more comfortable, more secure, uninterrupted, and vastly safer means to hand walk from an easily reached initial starting position, to a position near the distal end of the treatment table where the patient is able to lower herself/himself face down onto the device. As shown below, prone breast treatment tables typically include a head/upper arm support area, a chest support area, an abdominal support area, and a hip/thigh support area. However, to accommodate breast treatment, lateral portions of the chest support area are removed, thus effectively creating openings or gaps on the lateral edges of the table, between the head/arm support area and the abdominal support area. With respect to such gaps or openings, the hand rail provides a reassuring and intuitive bridging. Providing the user an uninterrupted, secure grasp for sliding her/his hands forward or back ensures a high level of continuous stability and safety that encourages confidence and reduces anxiety. In the event of balance loss, the patient is also better able to catch herself and help prevent a fall. This then also reduces the burden on the clinical technician to prevent a fall. As such the hand rails are attached to the device securely against forces in all directions. In order to avoid interferences in imaging or treatment, the hand rails are configured to allow repositioning clear of the imaging/treatment area, as shown in FIG. 2, either to be stored on the device alongside the patient or removed entirely.

Figure 1:
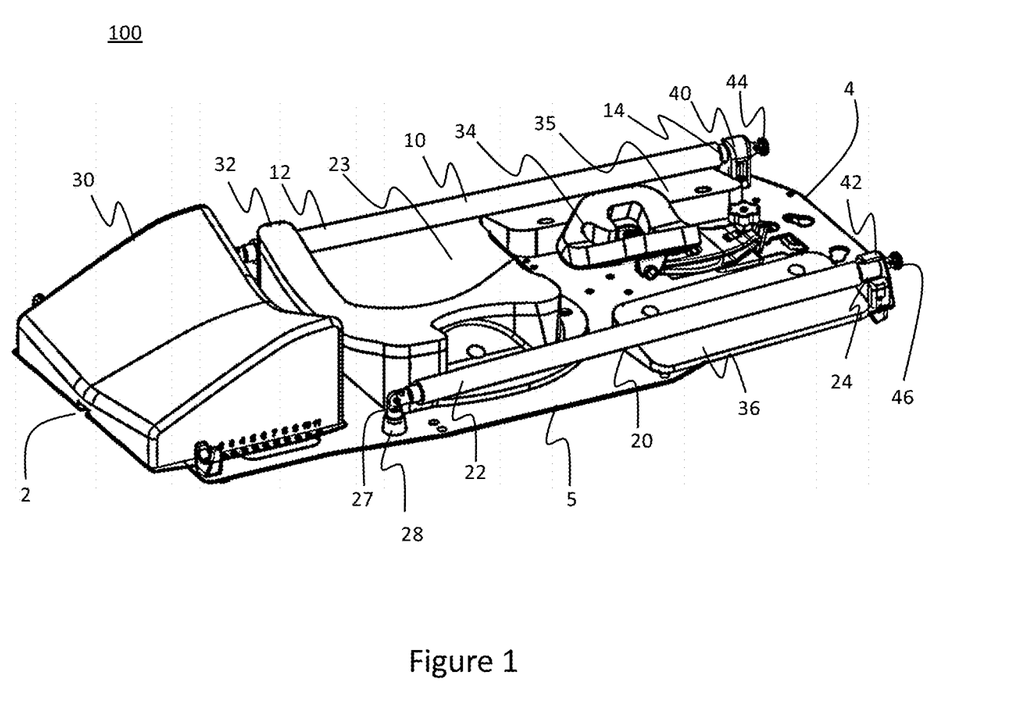
FIG. 1 a drawing of an exemplary patient table extension.

FIG. 1 is drawing of an exemplary prone breast treatment table extension 100. The table extension includes a base 5 having a proximal end 2 and a distal end 4, a longitudinally adjustable hip/thigh support pad 30, a chest support 32 having an opening 23 for imaging or treatment of the patient's left breast. The table extension also includes an adjustable head support 34 and upper arm supports 35, 36. The table extension also includes two hand rails 10, 20. Each handrail 10, 20 has a proximal end 12, 22 and a distal end 14, 24. In FIG. 1, the handrails 10, 12 are shown in the locked position for patient use. In this position, distal ends 14, 24 of the handrails 10, 12 are shown locked into receiving supports 40, 42, respectively. The supports 40, 42, include spring-loaded retractable locking pins 43 (one of which is shown in FIG. 2, in relation to receiving support 42), which may be retracted with knobs 44, 46, respectively, to remove the handrail distal ends 14, 24 from the locking supports 40, 42, respectively. Details of the locking pins are shown in cross section view FIG. 6. Other means of retaining the distal ends of the handrails include, for example, spring-loaded clips, flexible straps, and spring-loaded collars that fit over the ends of the handrail. Handrail 20 is supported at its proximal end 22 by a hinge 27. The hinge 27 is mounted on a rotatable pedestal 28, which is attached to the patient table base 5. The attachment may be configured to allow quick removal and replacement of the handrail and hinge. A corresponding version (not shown) of the exemplary treatment table for examination or treatment of the patient's right breast is arranged as shown in FIG. 1 except that opening 23 is on the right-hand side of the table with respect to the prone patient. A similar hinge and rotatable pedestal (obscured in FIG. 1) attach the proximal end 12 of the left hand-rail 10 to the base 5 of the patient table extension.

Figure 2:
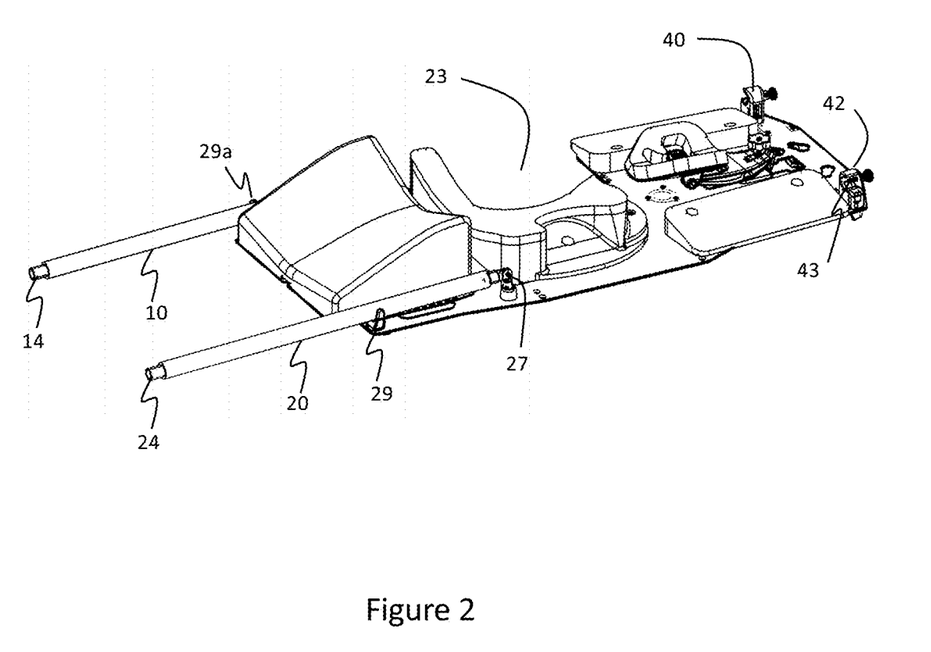
FIG. 2 is another drawing of the exemplary patient table extension of FIG. 1.

FIG. 2 is a drawing of the exemplary patient table extension 100 of FIG. 1 with the handrails 10, 20 disengaged from the receiving supports 40, 42, respectively. The handrails may be rotated about the hinges (hinge 27 shown for handrail 20) to a position away from the patient's upper body such that the examination/treatment cavity 23 is fully accessible by medical equipment (not shown). A receiving cradle 29 accepts the right handrail 20, when in the unlatched position. A corresponding receiving cradle 29a accepts the left handrail 10. Although not shown in FIG. 1 or 2, in some implementations, to transition from the engaged state in FIG. 1 to the disengaged state of FIG. 2, handrails 10, 20 may be rotated laterally and/or vertically about pedestals 28, which act as a pivot, in addition to vertically about hinge 27. This allows handrails 10, 20 to be repositioned without unnecessarily contacting a prone patient. The lateral rotation may also be useful to avoid any overhead equipment. In a further embodiment, the hinges may be replaced with springs. In a further embodiment, very stiff springs, matched to the patient's weight may be used to support the attached end of the handrails and may be used by the patient to lower herself onto the extension table. The handrail attachment mechanisms, whether rotatable pedestal or spring, at the proximal end may be releasably attached to the base 5 to allow the handrails 10, 20 to be fully removable. The attaching/releasing mechanism may be a cotter pin, a clip, spring-loaded pins fitting into mating slots or holes and the like.

Figure 3:
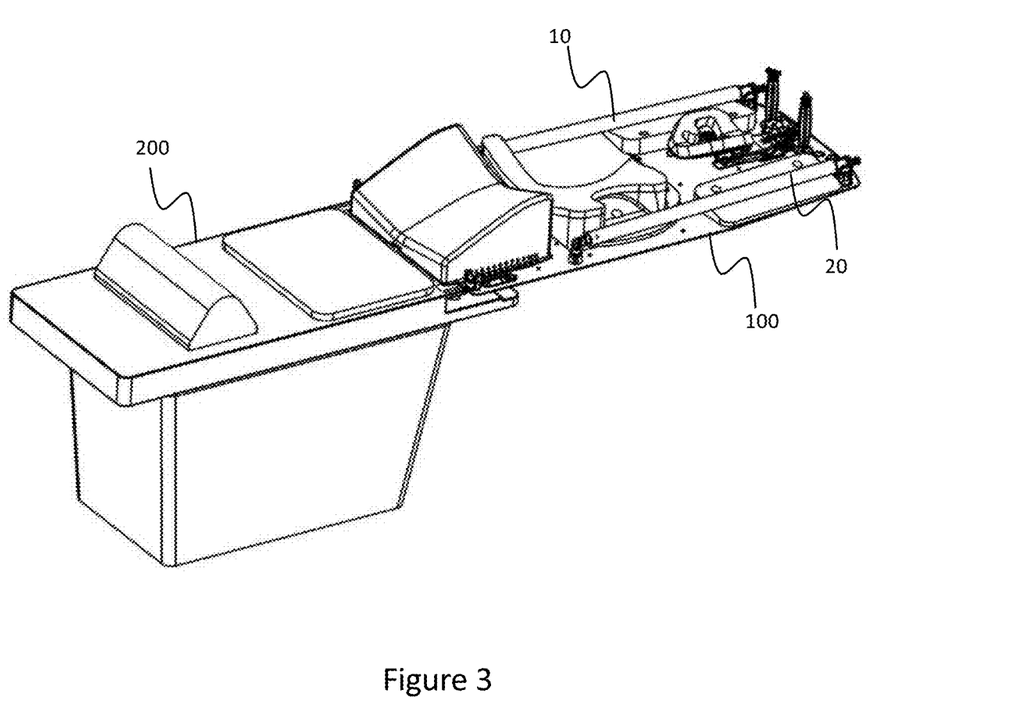
FIG. 3 is a drawing of the patient extension table of FIGS. 1 and 2 mounted on a table base.

FIG. 3, shows the table extension 100 mounted on a treatment table base 200. The patient kneels on the treatment table base 200 on which the table extension 100 is mounted with her hands grabbing the handrails 10, 20 and "walks" her way slowly from the proximal end 2 of the table extension towards the distal end 4. Bars 10, 20 provide a reassuring and intuitive place to put the hands, the left handrail 10 (right if using a device arranged for examination and/or treatment of the right breast) provides for sure and easy crossing of the large breast opening 23, and the handrails provide stability in all directions. In a further embodiment, the extension table may have only one moveable handrail on the side of the table extension having the opening and a fixed handrail on the other side. Having two handrails provides an advantage if the patient should start to fall to one side where she/he would be pulling up on one side and down the other to try and get back to a balanced position.

Figure 4:
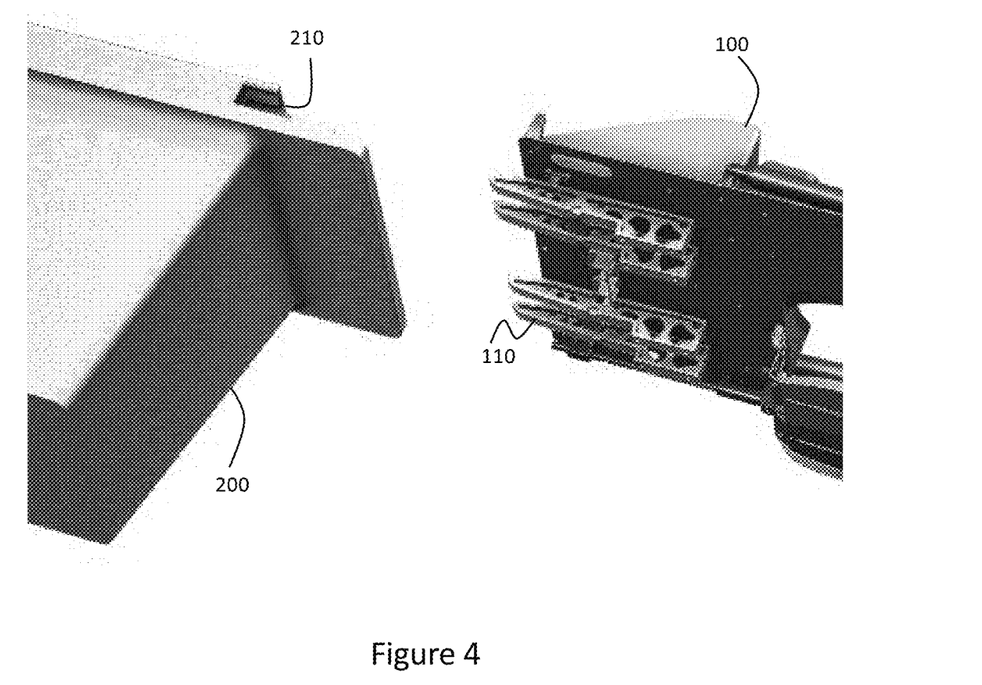
FIG. 4 is a drawing of partial views of the extension table and table base of FIG. 3.

FIG. 4 shows a partial view of a treatment table base 200 and a table extension 100. Four mounting rails 110 on the underside of the table extension 100 fit into corresponding slots 210 on the table base and secure the table extension 100 to the base 200. A latch (not shown) may be included on the table base to lock the mounting rails when fully inserted. Additionally, or alternatively, a latch (not shown) may be included on the table extension 100 to lock the extension to the base 200.

Figure 5:
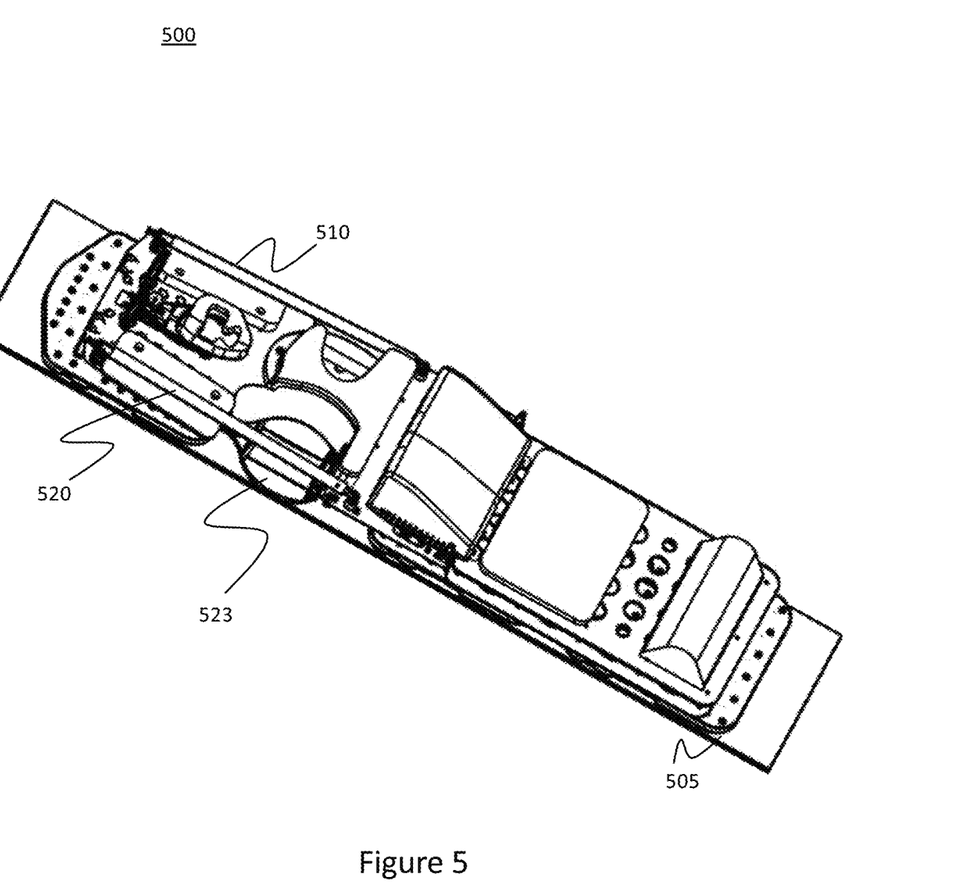
FIG. 5 is a drawing of an exemplary patient table for use in a computed tomography (CT) scanner.

FIG. 5 shows a patient treatment couch-top overlay 500, having handrails 510, 520 for use in computed tomography (CT) scanners. The overlay 500, in contrast to extension 100 described above in relation to FIGS. 1-4, is not an extension to a patient table as in FIGS. 1-4, but, rather, fits on top of a full body length treatment couch 505. The overlay 500 has an opening 523 for examination of the patient's left breast. Handrails 510 and 520 are releasable affixed to the overlay 500 in the same manner as described above for table extension 100. In a further aspect, for CT applications, table extension 100 may be used in combination with an adaptor that has a top surface and bottom surfaces flush with that of the extension.

Figure 6:
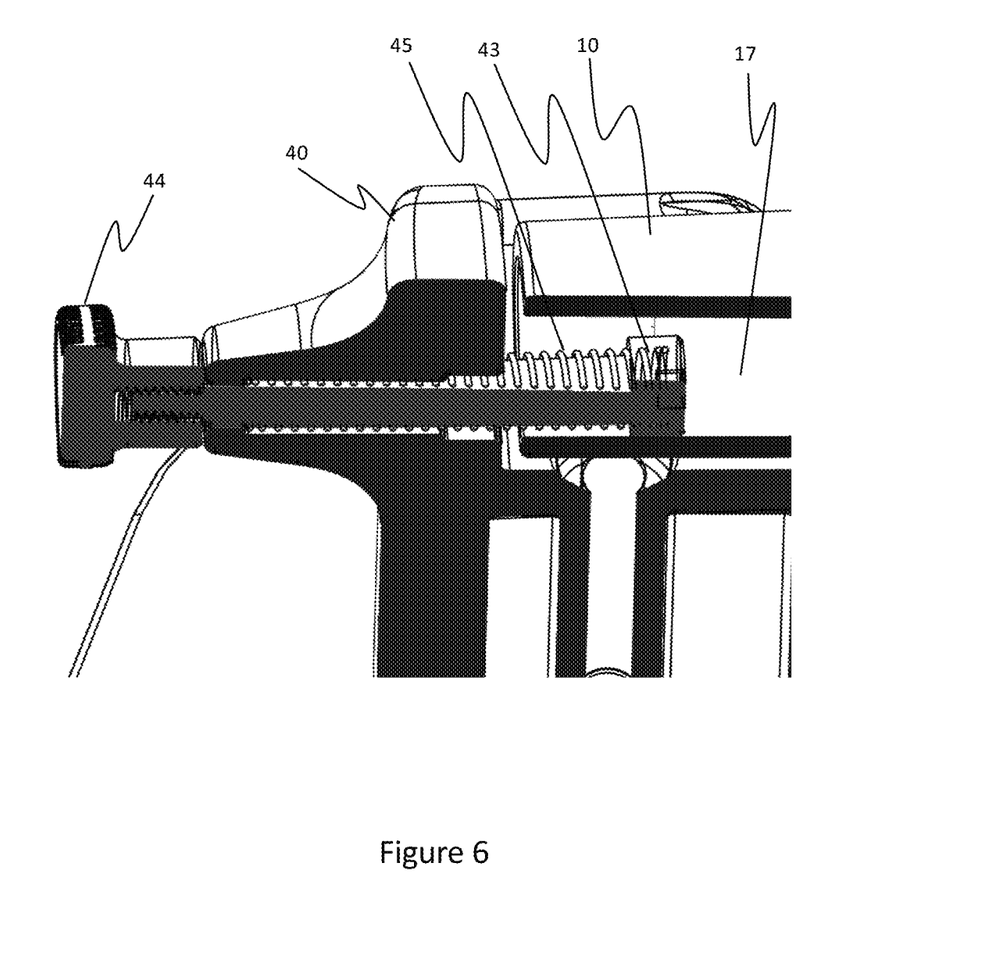
FIG. 6 is a cross section view of an exemplary spring-loaded retaining pin.

FIG. 6 is a cross section view of an exemplary spring-loaded locking pin 43 as described above with respect to FIG. 1. Locking pin 43 is part of an assembly that fits into cradle 40 for receiving the handrail 10. The pin 43 fits into a cavity 17 in the end of a handrail 10 when fully extended by the force of spring 45. Locking pin 43 can be retracted clear of the handrail cavity 17 by pulling on knob 44, thereby allowing the handrail 10 to be removed from the cradle 40.

Figure 7:
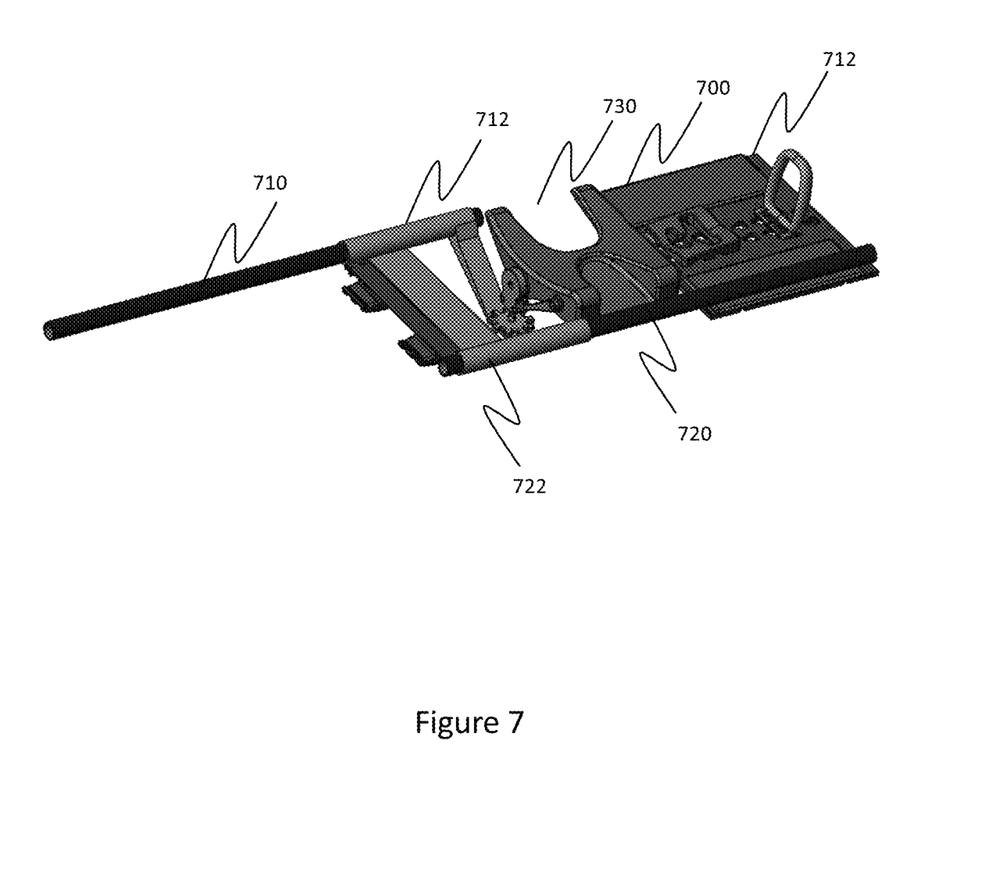
FIG. 7 is a drawing of a further embodiment of a patient table extension.

FIG. 7 shows another embodiment of a treatment table extension 700. In this embodiment, handrails 710, 720 are supported by tubes 712 and 722, respectively. The handrails 710, 720 can be slid away from the distal end 712 of the table extension 100 as shown with the top handrail 710, to allow for treatment or imaging equipment to access the open area 730. The handrails may be supported only by the tubes 712, 722 in a cantilevered fashion, as shown. Alternatively, the handrails 710, 720 may be supported at the distal end of the table 712 extension by a locking pin arrangement as shown, for example in FIG. 6. The tube supports 712, 722 may also be used in a couch-top overlay such as is shown in FIG. 5.

Figure 8:
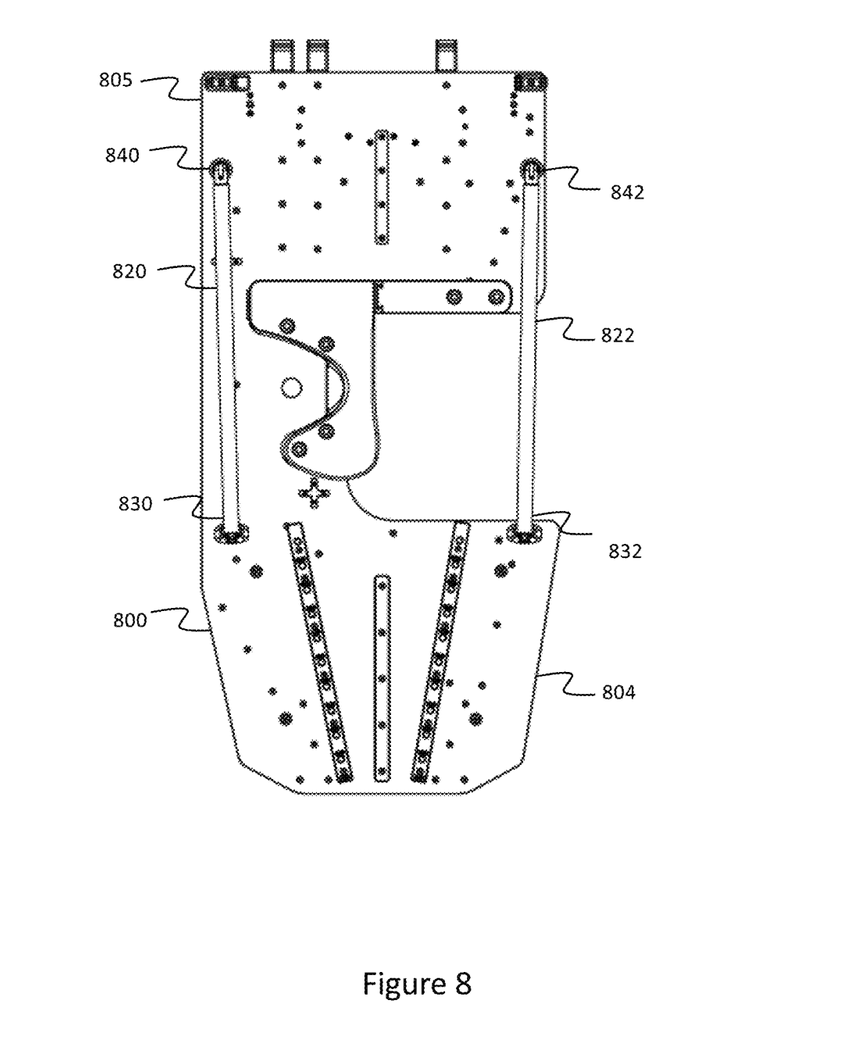
FIG. 8 is a drawing of another embodiment of an exemplary patient table extension.
Figure 9:
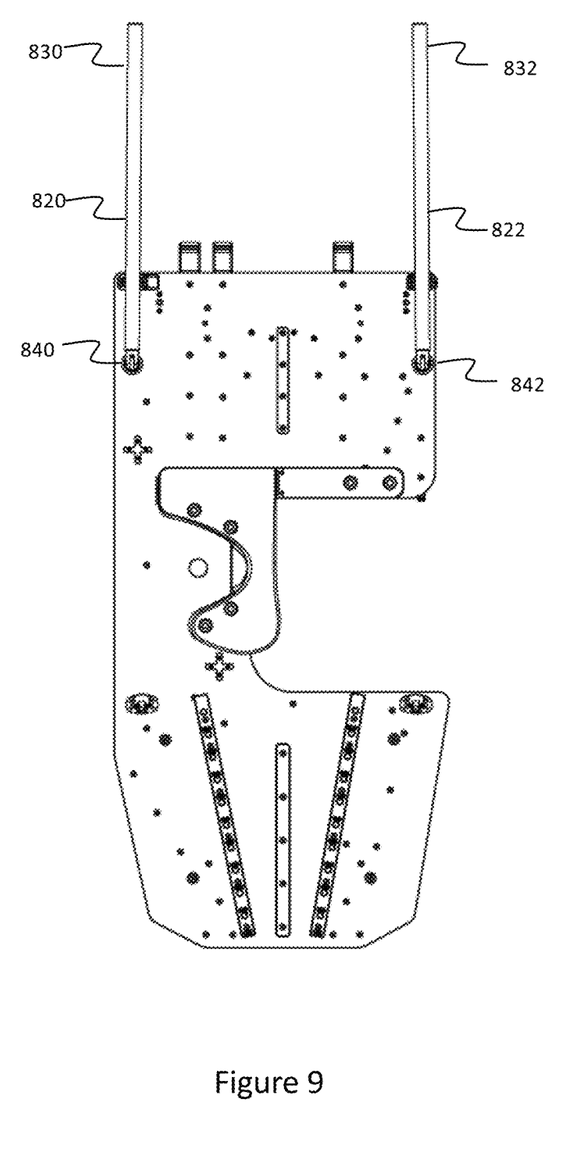
FIG. 9 is another drawing of the exemplary patient table extension of FIG. 8.

FIGS. 8 and 9 show another embodiment of a treatment table extension 800. In this embodiment, which may be a version of the treatment table extension shown in FIGS. 1 and 2, the handrails 820 and 822 are shorter than in FIGS. 1 and 2. The hand rails 820, 822 extend from the same pivot positions 830, 832 relative to the table extension base 805 as do the handrails 10, 20 shown in FIGS. 1 and 2. The distal ends 840, 842, of the handrails of FIGS. 8 and 9, however, do not extend all the way to the distal end 804 of the treatment table extension as do the handrails 10 and 20 in FIGS. 1 and 2. When laying down, the patients tend to rest their arms on top of the handrails 820, 822. This impedes moving the hand rails out of the way to their inferior positions (as shown in FIG. 9) for treatment. Shorter hand rails reduce the tendency for patients to rest their arms and as a result make it easier to move the handrails 820, 822 to their inferior positions for treatment.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A patient treatment table extension for imaging and treatment of a prone patient's breast, comprising:
   a planar base having right and left sides, proximal and distal ends and an opening for either a right or left breast on a respective left or right side of said base and located between said proximal and distal ends;
   a chest support located adjacent said opening; and
   at least one handrail located on said side having said opening side and extending from said distal end to said proximal end,
   wherein each of said at least one handrail is mounted to said planar base by a hinge at said proximal end and is restrained by a releasable mount at said distal end, said hinge configured to allow said handrail to be raised at said distal end and rotated toward said proximal end.

2. The patient treatment table extension of claim 1, wherein the at least one handrail comprises a first handrail located on the left side of the planar base and a second handrail located on a right side of the planar base, and wherein each respective hinge is mounted to a pivot configured to allow said first or second handrail to be rotated away from the side of said planar base.

3. The patient treatment table extension of claim 2, wherein said pivot is releasably attached to said planar base to allow removal and replacement of said handrail.

4. The patient treatment table extension of claim 1, wherein said releasable mount comprises a spring-loaded pin configured to mate into an opening at said distal end of said handrail.

5. The patient treatment table extension of claim 1, further comprising:
receiving cradles at said proximal end on said left and right sides of said planar base, said receiving cradles configured to retain first and second handrails when rotated away from said releasable mount.

6. The patient treatment table extension of claim 1, wherein the at least one handrail comprises a first handrail located on the left side of the planar base and a second handrail located on a right side of the planar base.

7. The patient treatment table extension of claim 1, wherein the releasable mount comprises a spring-loaded clip, a flexible strap, or a spring-loaded collar.

8. A patient treatment table comprising:
a treatment table base, and
a treatment table extension,
wherein said treatment table extension is removably attached to said treatment table base,
said treatment table extension having a planar base having right and left sides, proximal and distal ends and an opening for either a right or left breast on a respective left or right side of said base and located between said proximal and distal ends;
a chest support located adjacent said opening; and
at least one handrail located on said side having said opening side and extending from said distal end to said proximal end,
wherein each of said at least one handrail is mounted to said planar base by a hinge at said proximal end and is releasably restrained by a device at said distal end, said hinge configured to allow said handrail to be raised at said distal end and moved toward said proximal end.

9. The patient treatment table of claim 8, wherein the at least one handrail comprises a first handrail located on the left side of the planar base and a second handrail located on a right side of the planar base, and wherein each respective hinge is mounted to a pivot configured to allow said first or second handrail to be rotated away from the side of said planar base.

10. The patient treatment table of claim 9, wherein said pivot is releasably attached to said planar base to allow removal and replacement of said handrail.

11. The patient treatment table of claim 8, wherein said device comprises a spring-loaded pin configured to mate into an opening at said distal end of said handrail.

12. The patient treatment table of claim 8, further comprising:
receiving cradles at said proximal end on said left and right sides of said planar base, said receiving cradles configured to retain first and second handrails when rotated away from said device.

13. The patient treatment table of claim 8, wherein the at least one handrail comprises a first handrail located on the left side of the planar base and a second handrail located on a right side of the planar base.

14. The patient treatment table of claim 8, wherein the device comprises a spring-loaded clip, a flexible strap, or a spring-loaded collar.

15. A patient treatment table overlay for imaging and treatment of a prone patient's breast or chest area, comprising:
a planar base having right and left sides, proximal and distal ends and an opening for either a right or left breast on a respective left or right side of said base and located between said proximal and distal ends;
a chest support located adjacent said opening; and
at least one handrail located on said side having said opening side and extending from said distal end to said proximal end,
wherein each of said at least one handrail is mounted to said planar base by a hinge at said proximal end and is releasably restrained by a device at said distal end, said hinge configured to allow said handrail to be raised at said distal end and rotated toward said proximal end.

16. The patient treatment table overlay of claim 15, wherein the at least one handrail comprises a first handrail located on the left side of the planar base and a second handrail located on a right side of the planar base, and wherein each respective hinge is mounted to a pivot configured to allow said handrail to be rotated away from the side of said planar base.

17. The patient treatment table overlay of claim 15, wherein said device comprises a spring-loaded pin configured to mate into an opening at said distal end of said handrail.

18. The patient treatment table overlay of claim 15, further comprising:
receiving cradles at said proximal end on said left and right sides of said planar base, said receiving cradles configured to retain first and second handrails when rotated away from said releasable mount.

19. The patient treatment table overlay of claim 15, wherein said pivot is releasably attached to said planar base to allow removal and replacement of said handrail.

20. The patient treatment table overlay of claim 15, wherein the device comprises a spring-loaded clip, a flexible strap, or a spring-loaded collar.

* * * * *